United States Patent [19]

Atherton

[11] 4,036,807
[45] July 19, 1977

[54] FLUORINE-CONTAINING ORGANOSILICON COMPOUNDS

[75] Inventor: John Heathcote Atherton, Manchester, England

[73] Assignee: Imperial Chemical Industries Limited, London, England

[21] Appl. No.: 509,026

[22] Filed: Sept. 24, 1974

Related U.S. Application Data

[62] Division of Ser. No. 339,764, March 12, 1973, Pat. No. 3,859,320.

[30] Foreign Application Priority Data

May 22, 1972 United Kingdom ............... 23888/72

[51] Int. Cl.² .................................................. C08K 9/06
[52] U.S. Cl. ............................. 260/42.15; 260/42.27; 260/42.55
[58] Field of Search ........................ 260/42.27, 42.15

[56] References Cited

U.S. PATENT DOCUMENTS 3,880,798   4/1975   Deem ................... 260/42.16

Primary Examiner—James H. Derrington
Attorney, Agent, or Firm—Cushman, Darby & Cushman

[57] ABSTRACT

Silanes and siloxanes having at least one group of the general formula

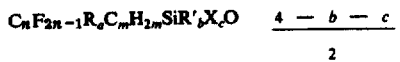

$$C_nF_{2n-1}R_aC_mH_{2m}SiR'_bX_cO_{\frac{4-b-c}{2}}$$

where R is a divalent group, R' is a monovalent hydrocarbon group, X is a hydrolyzable group, $n$ is 8, 10 or 12, $a$ is 0 or 1, $m$ is 2, 3 or 4, $b$ is 0, 1 or 2, $c$ is 0, 1, 2 or 3 and $b + c$ is not greater than 3, and uses thereof e.g. in surface treatment of glass fibres.

4 Claims, No Drawings

FLUORINE-CONTAINING ORGANOSILICON COMPOUNDS

This is a division of application Ser. No. 339,764 filed Mar. 12, 1973, now U.S. Pat. No. 3,859,320.

This invention relates to fluorine-containing organosilicon compounds and more particularly to silanes and siloxanes having one or more unsaturated fluorocarbon substitued groups therein.

A number of silanes or siloxanes are known or have be proposed which contain fluorocarbon groups. In all of these the fluorocarbon group has been a saturated group. Because of their nature these materials suffer from various disadvantages, for example, such a high cost.

According to the present invention a new class of silanes and siloxanes comprising at least one group of the general formula:

$$C_nF_{2n-1}R_aC_mH_{2m}SiR'_bX_cO_{\frac{3-b-c}{2}}$$

where R is a divalent group, R' is a monovalent hydrocarbon group, X is a hydrolysable group, $n$ is 8, 10 or 12, $a$ is 0 or 1, $m$ is 2, 3 or 4, $b$ is 0, 1 or 2, $c$ is 0, 1, 2 or 3 and $b + c$ is not greater than 3.

The siloxanes of our invention may contain in addition to the above specified groups, units of one or more of the general formulae:

$$Z_3SiO_{1/2}, Z_2SiO, ZSiO_{3/2}, SiO_2, Z''SiO \text{ and } HZ_2SiO_{1/2}$$

where Z is a monovalent hydrocarbon group of the kind well known in siloxanyl units. It is in fact frequently preferred that Z be a methyl group.

The group R may be oxygen, an alkylene group having not more than 8 carbon atoms, a polyoxyalkylenediol residue or a phenyleneoxy or substituted phenyleneoxy group. Monovalent substituents which may be present in the phenyleneoxy group include alkyl and alkoxy groups and halogen atoms. Divalent substituents which may be present alone or in addition include sulphonamido and carboxyl groups to link the phenyleneoxy group to the group $C_mH_{2m}$.

The groups R' may be alkyl, aryl, alkaryl, aralkyl, or cycloalkyl groups, for example, such as methyl, ethyl, propyl or phenyl groups. It is in general preferred that the groups R' be methyl groups.

The group X may be, for example, a halogen atom, an alkoxy group, a substituted alkoxy group or a polyoxyalkylene group. Suitable groups include, for example, fluorine, chlorine, bromine, methoxy, ethoxy, propoxy, butoxy, methoxyethoxy, ethoxyethoxy, phenoxy and 2-(N,N-dimethylamino)ethoxy groups. It is normally preferred that the groups X be chlorine, methoxy or ethoxy groups.

In one method of preparing the compounds of our invention, where R is a phenyleneoxy group or substituted phenyleneoxy group, an unsaturated tetrafluoroethylene oligomer of general formula:

$$C_nF_{2n}$$

where $n$ is 8, 10 or 12 may be first reacted with an allylphenol or substituted allylphenol after which the compound so prepared is reacted with a silane or siloxane containing at least one siliconbonded hydrogen atom.

The reaction with the allylphenol or substituted allylphenol may be carried out by stirring the reactants together in presence of a solvent such as dimethylformamide and an acid acceptor such as triethylamine. The product of this reaction is then reacted with a compound containing silicon-bonded hydrogen in presence of a suitable catalyst. These products may also be prepared by first preparing a compound of the oligomer and a sulphonyl chloride substituted phenol, e.g. as described in U.K. Patent Application No. 8295/71, and reacting this with a suitable γ-aminoalkyl silane or siloxane, e.g. γ-aminopropyltriethoxysilane or alternatively by reacting the phenol/oligomer compound with an amino-olefin such as 3-aminopropyl-1-ene and then reacting the product with a silane or siloxane containing at least one silicon-bonded hydrogen atom.

In another method of preparing the compounds of our invention, where $a$ is 0, a tetrafluoroethylene oligomer may be reacted with an alkenyl magnesium bromide and the reaction product thereafter reacted with a silane or siloxane containing at least one silicon-bonded hydrogen atom. The reaction may be carried out by simultaneously adding the alkenyl bromide and a tetrafluoroethylene oligomer to a stirred suspension of magnesium in diethyl ether and thereafter reacting the product so obtained with the silicon compound.

The reaction of the allyl fluoro compound with the silane or siloxane containing at least one silicon-bonded hydrogen atom may be carried out in known manner and in the presence of a catalyst of the kind known to be suitable for such reactions. Suitable catalysts include, for example, chloroplatinic acid, cyclohexene platinum-(II)-chloride and bis(diethylsulphide) platinum-(II)chloride.

Suitable silanes for use in this reaction include, for example, trichlorosilane, methyl-dichlorosilane, dimethylchlorosilane, trimethoxysilane, triethoxysilane, methyldiethoxysilane and dimethylmethoxysilane.

The siloxanes of our invention can be made either directly or by hydrolysis of a silane of our invention alone or in presence of one or more other hydrolysable silanes. They may also be produced by equilibration.

The products of our invention have a wide variety of uses. For example, they may be used to render the surface of glass hydrophobic and oleophobic, and are thus useful for the treatment of glazing in agricultural buildings e.g. greenhouses, and in the treatment of glass fibres for use as filters for liquids and gases. They are also of value as antifoam agents especially in non-aqueous systems and as release agents.

Flurocarbon derivatives containing silane or siloxane groups may be used for the treatment of fillers e.g. glass fillers in the manufacture of filled granular grades of fluorocarbon polymers. Preferably the filler is treated with a solution of the derivative in an organic solvent to coat the filler with the derivative and make it hydrophobic prior to agglomerating it with the fluorocarbon polymer from an aqueous medium.

Fluorocarbon derivatives containing a $C_nF_{2n-1}$ group where n=8, 10 or 12 linked to a group of formula:

$$SiR_bX_cO_{\frac{3-b-c}{2}}$$

e.g. compounds comprising at least one group of the formula:

where R, R', X, n, a, m, b and c are as defined above may be used. Particularly useful derivatives are compounds of the formulae:

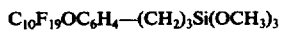

and

The formation of relatively small size agglomerates of a fluorocarbon polymer and filler is important in moulding technology as it enables free flowing filled particles to be formed from poorly flowing polymer. The particles can be more readily handled than unagglomerated polymer and filler e.g. in automatic mould machinery.

By making the filler particles hydrophobic with a surfactant which will withstand the washing conditions experienced in agglomeration from an aqueous medium, as further described below, the successful agglomeration of polymer and filler is facilitated. In practical terms this means that a substantial proportion of the filler charged to the wash vessel will under suitable conditions be agglomerated with the fluorocarbon polymer. Thus waste of filler will be minimised and the composition of the agglomerated product will be predictable from the relative amounts of polymer and filler charged. It has thus proved a valuable discovery that fluorocarbon derivatives as described above can be used to treat fillers successfully in this agglomeration method.

Fluorocarbon polymers in granular form are made by methods well known in the art for example by polymerising monomer in an aqueous medium in the absence of a stabilizing amount of emulsifying agent. The polymer recovered is usually comminuted e.g. by milling, before a filler is incorporated into it. The fluorocarbon polymers include granular grades of polytetrafluoroethylene (PTFE) and copolymers of tetrafluoroethylene with up to 15% by weight of other monomers such as ethylene, vinyl chloride and hexafluoropropene.

The fillers that may be treated prior to incorporation into the fluorocarbon polymer in addition to glass include metallic fillers such as aluminium, bronze, copper, nickel and iron and mineral fillers such as asbestos, mica, silica and talc. In an agglomeration from an aqueous medium there is generally no need to treat fillers which are already hydrophobic e.g. graphite, to assist in their agglomeration with the polymer.

In carrying out an agglomeration from an aqueous medium the granular polymer and filler, both in fine particle form, the filler having been treated with the fluorocarbon derivative, may be charged to a washing vessel in which they are agitated with water by suitable stirring means until agglomerates of a suitable size and containing both the polymer and filler are formed. The agglomerates are subsequently recovered from the vessel and dried. A suitable agitation period is from two to four hours at 60° to 90° C. Milled granular PTFE of 20-25 μm mean particle size is a suitable form of polymer to use e.g. with finely divided glass fibres.

Our invention is further illustrated by the following examples in which all parts and percentages are by weight.

EXAMPLE 1

1500 parts of tetrafluoroethylene pentamer, 1300 parts of dimethylformamide, 482 parts of o-allylphenol and 380 parts of triethylamine were stirred together for 28 hours at 25° C. The lower layer was then allowed to settle, separated, washed successively with 1500 parts of 5% aqueous sulphuric acid and 1500 parts of water, and then dried azeotropically by refluxing with toluene under a Dean-Stark separator. In addition to water, 262 parts of tetrafluoroethylene pentamer were removed via the Dean-Stark separator. Toluene was distilled off and the residue fractionated in vacuo. 1168 parts of the compound

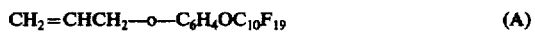

were obtained, b.p. 83°/0.3mm.

Analysis: Calc. for $C_{19}H_9F_{19}O$ C, 37.1; H, 1.47%. Found: C, 37.0, H, 1.47, 1.39%.

123 parts of compound A and 0.046 part of bis-diethylsulphide platinum(II)chloride were heated to 120° C and 60 parts of trichlorosilane added dropwise. Reflux was maintained for 30 minutes. Vacuum distillation yielded 140 parts of $Cl_3Si(CH_2)_3$—o—$C_6H_4O.C_{10}F_{19}$ having a neutralisation equivalent of 253. Redistillation yielded an analytical sample, b.p. 135/0.5mm. (Found: C, 30.3, 29.9; H, 1.24, 1.19; F, 47.9, 48.7%. $C_{19}H_{10}Cl_3F_{19}OSi$ requires C 30.4; H, 1.3; F, 48.2%; neutralisation equivalent 250).

EXAMPLE 2

123 parts of compound A and 0.046 part of bis(diethylsulphide) platinum(II)chloride were heated to 120° C and 50 parts of methyldichlorosilane added dropwise over a period of 5 minutes. The mixture was refluxed for 1¼ hours and then distilled in vacuo. There were thus obtained 92.5 parts of $MeCl_2Si(CH_2)_3$—o—$C_6H_4OC_{10}H_{19}$, b.p. 107°/0.05 mm.

Found: C, 33.0, 32.9; H, 1.85, 1.85; Cl, 9.85, 9.70%. Calc. for $C_{20}H_{13}Cl_2F_{19}OSi$: C, 32.9; H, 1.8; Cl, 9.7%.

EXAMPLE 3

A mixture of 281 parts of compound A, 300 parts of toluene and 0.125 part of bis(diethylsulphide) platinum-(II) chloride was heated to reflux. 66.6 parts of trimethoxysilane were added dropwise to the refluxing solution, which was maintained at reflux for 6¼ hours after the addition was complete. Distillation in vacuo yielded 232 parts of $(MeO)_3Si(CH_2)_3$—o—$C_6H_4OC_{10}F_{19}$, b.p. 124°-125°/0.05 mm.

Found: C, 36.2, 36.3; H, 2.42, 2.33; —OMe, 12.1, 12.4%; Calc. for $C_{22}H_{19}F_{19}O_4Si$; C, 35.9; H, 2.6; OMe, 12.6%.

EXAMPLE 4

222 parts of 1,1,1,3,5,5,5,-heptamethyltrisiloxane, 614 parts of compound A, 0.5 part of bis(diethylsulphide) platinum(II) chloride and 210 parts of toluene were heated under reflux for 30 minutes. Infra-red analysis of the mixture showed that no Si—H containing material was present. Removal of volatile materials left a residue of 800 parts of the compound $(Me_3SiO)_2Si(Me)CH_2CH_2CH_2$—o—$C_6H_4OC_{10}F_{19}$, corresponding to 96% of theory. An analytical sample was obtained by distillation in vacuo. b.p. 142°/0.4 mm.

(Found: C, 37.3, 37.0; H. 3.69, 3.68%. $C_{26}H_{31}F_{19}O_3Si_3$ requires C, 37.3; H, 3.74%).

EXAMPLE 5

720 parts of the product of Example 2 were dissolved in 2500 parts of acetone and 500 parts of water added. When the exothermic reaction had subsided the mixture was heated under reflux for 30 minutes, after which all volatiles were distilled off to a final pressure of 0.5 mm. Hg at 100° C. The product was a clear viscous liquid at 100° C, becoming a highly viscous fluid at 20° C. It was a polysiloxane containing the repeating unit.

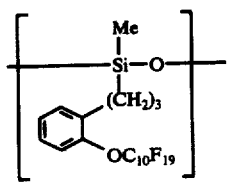

(Found: C, 35.7, 35.3; H, 1.50, 1.80; Si, 4.18, 4.45%; $C_{20}H_{13}F_{19}O_2Si$ requires C, 35.6; H, 1.9; Si, 4.2%.

EXAMPLE 6-10

Five substituted polysiloxanes have the formula

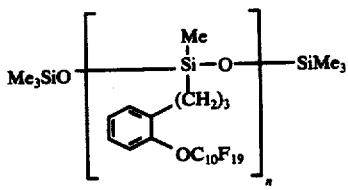

wherein n was 8, 25, 50, 98 and 200 were prepared as follows.

The polysiloxane $Me_3SiO(SiMeHO)_nSiMe_3$, 1.7 parts of bis (diethylsulphide) platinum(II)chloride, 500 parts of compound A and 1000 parts of toluene were heated to reflux. A lower layer separated out a few minutes after reflux was established. The mixtures were heated under reflux for 4 hours, then solvent was removed on a rotary evaporator. Theoretical yields were obtained. Parts of starting polysiloxane used are given in Table 1.

TABLE 1

| Example | n | Parts of Polysiloxane |
|---|---|---|
| 6 | 8 | 59.9 |
| 7 | 25 | 48.8 |
| 8 | 50 | 46.5 |
| 9 | 98 | 45.2 |
| 10 | 200 | 44.6 |

A foaming solution was prepared comprising a 2% solution in perchloroethylene of a mixture of butyl titanate (3 parts), a methylpolysiloxane copolymer containing $Me_3SiO_{1/2}$ and $SiO_2$ units in the ratio 1.2:1 (3 parts), a dimethylpolysiloxane having a viscosity of 300 cS at 25° C (3 parts) and a dimethylpolysiloxane having a viscosity of 30,000 cS at 25° C (1 part). The siloxanes of examples 6-10, and a cyclic siloxane F

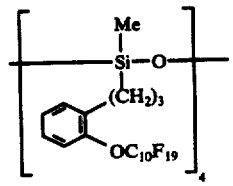

(F)

were tested for defoaming activity towards this solution. An aliquot of the foaming solution was treated with 50 ppm. of the siloxane as a 1% solution in $CFCl_3$. The solution was shaken for 30 seconds and the time needed for the foam to break was noted and is given in Table II.

TABLE II

| Siloxane | Defoam time (sec.) |
|---|---|
| 6 | 12.8 |
| 7 | 12.5 |
| 8 | 17.6 |
| 9 | 17.1 |
| 10 | 21.4 |
| F | 12.1 |

In the absence of antifoam the foam was stable for > 5 minutes.

EXAMPLE 11

Preparation of

Reagents

269 g (0.4m)

obtained by a method described in UK Patent Application No. 8295/71

| | | |
|---|---|---|
| (γ amino propyl triethoxy silane) | 82.8g | (0.4m) |
| Sodium carbonate | 43g | (0.4m) |
| "Arcton" 113 (1,1,2-trifluoro-1,2,2-trichloroethane) | 1.2 liters | |

The amino silane in Arcton 113 (200 ml) was added dropwise to a stirred solution of the sulphonyl chloride in Arcton (1 litre) containing the suspended sodium carbonate. On complete addition the mixture was stirred for an additional 30 minutes at 25° C, filtered and evaporated to dryness to yield 337g of a colourless viscous liquid. The fluorosilane so obtained was then distilled under high vacuum to provide an analytical sample.

Spectroscopic measurements were in complete agreement with the structure

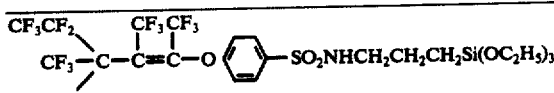

Spectroscopic Measurements
Mass No parent ion observed
Ions produced at
  m/e = 814 corresponding to parent - $C_3H_7$
  " = 842 corresponding to parent - $CH_3$ -continued " = 220 corresponding to parent NH(CH₂)₃Si(OC₂H₅)₃
" = 174 corresponding to parent loss of C₂H₅OH from ion m/e 220
" = 163 corresponding to parent Si(OC₂H₅)₃
NMR - ¹⁹F peaks at following positions in ppm
Solvent CCl₄

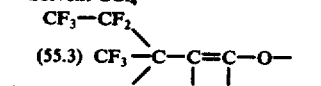

(55.3) CF₃—C—C=C—O—
(78.8) CF₃CF₂    CF₃CF₃
(104.0) (41.3)(58.1)

H' peaks at following positions in ppm

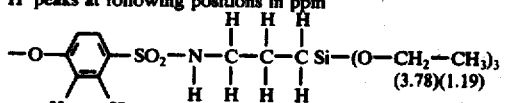

(3.78)(1.19)

(7.10) (8.00) (6.08) (2.96) (1.64) (0.56)

The same compound was also prepared by the following sequence of reactions:

C₁₀F₁₉O—⟨ ⟩—SO₂Cl + NH₂—CH₂—CH.=CH₂

C₁₀F₁₉O—⟨ ⟩—SO₂NHCH₂CH=CH₂ bis(diethyl sulphide) platinum II chloride

(EtO)₃SiH

C₁₀F₁₉O—⟨ ⟩—SO₂NHCH₂—CH₂—Si(OEt)₃

EXAMPLE 12

Reagents C₁₀F₁₉O—⟨ ⟩—SO₂NH(CH₂)₃Si(OEt)₃

|  |  |
|---|---|
|  | 43.5g(0.05M) |
| Potassium hydroxide | 0.2g |
| Isopropanol | 200 ml |

A solution of the fluorosilane (prepared as described in Example 11) in isopropanol containing finely-ground potassium hydroxide was stirred at 25° C for 15 hours. The solvent was then removed in vacuo and the polysiloxane dissolved in 1,1,2,-trifluoro-1,2,2-trichloroethane. The resultant solution was washed with water, dried and concentrated to afford a 20% w/w solution which was useful for coating glass surfaces.

EXAMPLE 13

48 mls of a 0.3% solution of a compound made in accordance with Example 11 dissolved in 1,1,2-trifluoro 1,2,2-trichloroethane was mixed with 400 g of Owens-Corning Fibreglass 709 glass fibre.

The mixture consisting essentially of the glass fibres dampened with the solution was dried at 120° C for 16 hours in an oven with a suitable solvent extraction system. 325 g of dried coated glass fibres were mixed with 875 g of PTFE (Fluon G163 obtained from Imperial Chemical Industries Limited). The 1.2 kg mixture was charged to a 30 liter vessel with 20 liters of water at less than 25° C. A stirrer in the vessel ran at 450 rpm while the temperature wash raised to 80° C, and maintained at this temperature for 2 hours. The temperature was allowed to fall to less than 30° C, the stirrer stopped and the slurry from the vessel discharged to a dewatering table with 400 μm openings. The product retained on the table was dried for 2 hours at 200° C, and baked for 3 hours at 280° C. The cool product was sieved through a sieve having 1000 μm openings. The product passing through the sieve was in the form of smooth glass filled PTFE agglomerates with a measured glass content of 24.9%. Thus of the 27% of the glass originally present, only slightly in excess of 2% had failed to be agglomerated with the PTFE and the process was therefore considered successful.

EXAMPLE 14

Example 13 was repeated except that the solution mixed with the 400 g of glass fibre consisted of 18 mls of a 1% solution of the compound prepared as described in Example 3 to which had been added 31 mls of a 1% aqueous solution of acetic acid. The product passing through the sieve having 1000 μm openings was an agglomerated glass filled PTFE with a measured glass content of 24.8%. The agglomerates had smooth surfaces. The process was therefore rated successful.

What we claim is:

1. A method of preparing a filled fluorocarbon polymer from a filler and a granular fluorocarbon polymer, both in powder form, comprising treating the filler with a fluorocarbon derivative and agglomerating the filler together with the polymer from an aqueous medium, recovering the drying the agglomerate, the fluorocarbon derivative being an organosilicon compound of the general formula:

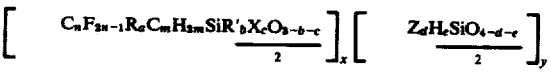

where R is a divalent group selected from the group consisting of oxygen, alkylene groups having not more than 8 carbon atoms, polyoxyalkylene diol residues, phenyleneoxy groups and phenyleneoxy groups containing substituents selected from the group consisting of lower alkyl and alkoxy groups and halogen atoms and in the case where R is a phenyleneoxy or a substituted phenyleneoxy group, the group R being optionally linked to the group $C_m H_{2m}$ via a group selected from the group consisting of sulphonamido and carboxyl groups, R¹ is selected from the group consisting of methyl and phenyl groups, X is selected from the group consisting of halogen atoms, lower alkoxy groups, substituted lower alkoxy groups and polyoxyalkylene groups, Z is selected from the group consisting of lower alkyl groups and phenyl, a is 0 or 1, b is 0, 1 or 2, c is 0, 1, 2, or 3, b + c is not greater than 3, d is 0, 1, 2 or 3, e is 0 or 1 and d + e is not greater than 3, n is 8, 10 or 12, m is 2, 3 or 4, x is a positive integer, when b + c is 3, y is 0, and when b + c is not greater than 2, y is a positive integer.

2. A method according to claim 1 wherein the fluorocarbon derivative is C₁₀F₁₉OC₆H₄—(CH₂)₃Si(OCH₃)₃ or C₁₀F₁₉OC₆H₄—SO₂—NH(CH₂)₃Si(OC₂H₅)₃.

3. A method according to claim 1 wherein the filler is treated with a solution of the fluorocarbon derivative to render it hydrophobic prior to mixing and agitating it with granular polytetrafluoroethylene in an aqueous medium.

4. Filled granular polytetrafluoroethylene wherein the filler is coated with a fluorocarbon derivative as defined in claim 1.

* * * * *